United States Patent [19]
Koch

[11] Patent Number: 6,102,037
[45] Date of Patent: Aug. 15, 2000

[54] RESPIRATION HUMIDIFIER

[75] Inventor: Jochim Koch, Ratzeburg, Germany

[73] Assignee: Dräger Medizintechnik GmbH, Germany

[21] Appl. No.: 09/130,278

[22] Filed: Aug. 6, 1998

[30] Foreign Application Priority Data

Feb. 28, 1998 [DE] Germany .............................. 198 08 590

[51] Int. Cl.$^7$ .................................................. A61M 16/00
[52] U.S. Cl. .................................. 128/203.26; 128/204.17; 128/201.13; 128/203.27; 128/203.16
[58] Field of Search ........................ 128/203.26, 203.27, 128/203.12, 203.16, 203.17, 204.14, 204.13, 204.17, 203.25, 204.18, 213.13

[56] References Cited

U.S. PATENT DOCUMENTS

| | | | |
|---|---|---|---|
| 3,871,373 | 3/1975 | Jackson . | |
| 4,038,980 | 8/1977 | Fodor . | |
| 4,750,483 | 6/1988 | Ankartross et al. | 128/203.26 |
| 4,770,168 | 9/1988 | Ruzz et al. | 128/203.12 |
| 4,773,410 | 9/1988 | Blackmer et al. | 128/203.16 |
| 4,829,998 | 5/1989 | Jackson | 128/203.12 |
| 5,172,686 | 12/1992 | Anthony | 128/203.16 |
| 5,243,973 | 9/1993 | Falb et al. | 128/203.27 |
| 5,390,665 | 2/1995 | Leach | 128/203.25 |
| 5,769,071 | 6/1998 | Turnbull | 128/203.12 |

FOREIGN PATENT DOCUMENTS

| | | |
|---|---|---|
| 0 567 158 A2 | 10/1993 | European Pat. Off. . |
| 0 716 861 A1 | 6/1996 | European Pat. Off. . |
| 25 16 496 C3 | 10/1976 | Germany . |
| 27 02 674 C3 | 7/1978 | Germany . |
| 23 45 677 C3 | 11/1982 | Germany . |
| 4105971A1 | 8/1992 | Germany .......................... 128/205.23 |
| 41 16 512 A1 | 11/1992 | Germany . |
| 41 30 724 A1 | 3/1993 | Germany . |
| 43 03 645 C2 | 8/1994 | Germany . |
| 43 12 793 C2 | 10/1994 | Germany . |
| 195 08 803 A1 | 9/1995 | Germany . |
| 196 02 077 A1 | 8/1996 | Germany . |
| 196 21 541 C1 | 4/1997 | Germany . |

OTHER PUBLICATIONS

Penlon Limited Aug. 1981 *Penlon Humidifier Instruction and Maintenance Manual* Penlon Manual.

*Primary Examiner*—John G. Weiss
*Assistant Examiner*—V. Srivastava
*Attorney, Agent, or Firm*—McGlew and Tuttle, P.C.

[57] ABSTRACT

A respiration humidifier has a metering device (3, 10) and an electrically heated evaporator (4), which is in connection with or can be connected to the metering device (3, 10) on its inlet side (E) and with a respiratory gas channel (5), through which respiratory gas can flow, on its outlet side (A). The metering device (3, 10) feeds the amount of water necessary for humidifying the respiratory gas to a predetermined relative humidity of the respiratory gas at a predetermined respiratory gas temperature to the evaporator (4) per unit of time as a function of the amount of respiratory gas flowing through per unit of time. The evaporator (4) provides water vapor with a temperature above 134° C., which heats the respiratory gas to the predetermined respiratory gas temperature on mixing with the respiratory gas to be humidified.

21 Claims, 5 Drawing Sheets

RESPIRATION HUMIDIFIER

FIELD OF THE INVENTION

The natural heating and humidification of the respiratory gas within the upper airways (nose, pharynx, bronchi) is bridged over by a breathing tube (tube) during the artificial respiration of adults and newborns. The current respirators themselves supply only dry and cold air or a dry and cold oxygen-air mixture. Using such devices, the patient would dry out during a prolonged mechanical respiration. In addition, the heat balance of premature and full-term newborn babies is strongly affected by the evaporation capacity associated with this, and these patients may develop hypothermia.

This is further compounded by the fact that the natural bacterial protective function of the upper airways is eliminated. Microorganisms present in the breathing tubes may be delivered unhindered directly into the lungs. This may lead to life threatening conditions precisely in the sick patients with impaired immune system.

The hygienic treatment of the airways by a respiratory air humidifier (respiration humidifier) is therefore of great significance.

BACKGROUND OF THE INVENTION

Respiration humidifiers generally used at present (as that described in, e.g., DE 195 08 803 A1) use a humidification chamber, in which heated water is distributed over a large surface. The respiratory gas is passed over this surface. During the contact with the water, the respiratory gas is heated and humidified. This system does not remain sterile, because it is in connection with both the ambient air and the returning water of condensation of the inspiration tube. In addition, this system has too high a compliance, which makes use difficult precisely in the case of premature and full-term newborn babies. The wish to integrate the respiration humidifier within the respirator is hindered by the size of the humidification chamber, as well as its position-dependent function.

The respiration humidifier described in DE 196 21 541 C1 has a membrane type humidifier with a hollow fiber module, which maintains the desired sterility of the water over a long time and also only has a small size. The drawback is that the breathing resistance is not negligible; it is 2 mbar at a respiratory gas flow rate of 60 L/minute. The breathing resistance is especially significant in cases in which the respirator fails and the patient must be supplied spontaneously via an emergency respirator. Excessively high breathing resistances cannot be overcome by the patient. Another drawback of this respiration humidifier is that the hollow fiber module has a wet surface on the respiration side, which may become contaminated with microorganisms after a certain time. These respiration modules must therefore be cleaned and sterilized or completely replaced as disposable parts at regular intervals. This leads to correspondingly high operating costs in the case of this system.

Another possibility of humidifying the respiratory gas is described in DE 43 03 645 C2. A sintered material is placed into a water bath having constant water level and heated. The respiratory gas sweeps past the sintered material, is heated and humidified. This system is intended for humidification in the case of insufflation, while the respiratory gas flow is constant. It is not suitable for respiration, because the humidity and the temperature cannot be controlled independently from one another. The breathing resistance and the compliance are too high. In addition, it is an open system from a hygienic viewpoint, both from the water supply side (with a float chamber, which is in connection with the ambient air), and from the respiratory gas side. The sintered surface may become contaminated very rapidly during periods of no respiration. The operating temperature is even favorable for the formation of microorganisms, and the sintered material with its fine pores is especially accommodating for microorganisms.

Another respiration humidifier has been known from DE-PS 27 02 674; water is boiled off in this humidifier in an evaporation chamber and the respiratory gas saturated with water vapor is sent to a superheater, which is controlled by the respiratory gas temperature of the patient system. The water supply is not separated from the outside air in a sterile manner. The evaporation chamber and the superheater are directly in the respiratory gas system and they must therefore be cleaned and sterilized before they are used for another patient. The design is correspondingly complex. The application of such a system to respirators has not proved successful, either.

Another prior-art respiration humidifier (see DE 43 12 793 C2) uses a heated evaporation chamber, to which water is fed via an injection needle. The evaporation chamber is maintained at a temperature of about 120° C.

A respiration humidifier has been known from DE-AS 25 16 496; this respiration humidifier has the drawback in practice that it is set at a constant evaporation capacity and operated in an uncontrolled manner. As a result, it heats the respiratory gas at different intensities, depending on the existing flow rate. The humidification of the respiratory gas is also uncontrolled; it is obtained from the heating power set and the flow rate. Either the respiratory gas is supersaturated, which correspondingly causes condensation into the condensate container provided for that purpose, or the respiratory gas is humidified insufficiently.

According to a completely different procedure, the water needed for the humidification is metered directly with a pump and is evaporated in a heating chamber (see, e.g., EP 0 716 861 A1, which shows a hose pump and a chamber for evaporating anesthetics). Even though such devices are technically more complicated, because they must actively meter the amount of water in proportion to the respiratory gas flow, they can be made very small, and they do not generate, in general, any additional breathing resistance.

Finally, DE 41 16 512 A1 describes an anesthetic evaporator, in which the respiratory gas flows through a heated, porous sintered material. If the anesthetic evaporator were used as a respiration humidifier, it would heat and humidify the breathing gas. However, separate heating and humidification of the respiratory gas is not possible in this arrangement. In addition, the respiratory gas would come directly into contact with the liquid, which could lead to problems in terms of sterility.

To complement the background information, one should mention the use of passive artificial noses (HME: Heat and Moisture Exchangers), which assume the bridged-over function of the natural upper airways (see DE 41 30 724 A1). These HMEs are adapted by necessity to the Y-piece of the breathing tube system, i.e., to the connection of the tube. The warm and humid air is stored in a moisture and heat exchanger during breathing out by the patient, and it is again released during breathing in. It was possible to markedly improve the efficiencies of such systems in the past years due to improved materials of the exchange surface. As a result, these systems have been increasingly used for the long-term respiration of adults. The technical effort is small.

They are, in general, disposable systems, which are removed and replaced with new ones at regular intervals. Yet, the humidification and heating capacity (line) of the systems is insufficient for especially ill patients. There have therefore been developments aimed at improving this passive system by an active humidification and heating (see, e.g., EP 0 567 158 A2); however, this is again technically complicated and leads to the need to lead many cables and tubes to the patient.

These artificial noses also have another serious drawback, which is inherent to the system: The breathing resistance is very high. Another exacerbating factor is that the systems very rapidly become contaminated by the aspiration of the patient and they also become clogged in this case. In many modes of respiration, the clogging of the artificial nose cannot be detected by the monitoring means, so that such systems may bring the patient into a hazardous situation, unless the internal pulmonary pressure (or esophageal pressure) is directly measured. However, being invasive measurements, such measurements are currently not accepted in practice and they also contradict the search for a simple system.

SUMMARY AND OBJECTS OF THE INVENTION

The primary object of the present invention is to provide a respiration humidifier that has a simple design, can be manufactured at low cost and makes possible the independent control of the respiratory gas temperature and of the relative humidity of the respiratory gas due to its concept.

According to the invention, a respiration humidifier is provided including a metering means and an electrically heated evaporator. The electrically heated evaporator is in connection on its inlet side with the metering means and is in connection with or can be connected on its outlet side to a respiratory gas channel, through which respiratory gas can flow. The metering means is designed to feed the amount of water needed to humidify the respiratory gas to a predetermined relative humidity of the respiratory gas at a predetermined respiratory gas temperature to the evaporator per unit of time as a function of the amount of respiratory gas flowing through per unit of time. The said evaporator is designed to provide water vapor with a temperature above 134° C., which heats the respiratory gas to the predetermined respiratory gas temperature on mixing with the respiratory gas to be humidified.

The respiration humidifier according to the present invention has a metering means and an electrically heated evaporator, which is in connection with or can be connected to the metering means on its inlet side and with a respiratory gas channel, through which respiratory gas can flow, on its outlet side. The metering means is designed to feed the amount of water needed for humidifying the respiratory gas to a predetermined relative humidity of the respiratory gas at a predetermined respiratory gas temperature per unit of time to the evaporator. This amount of water per unit of time depends on the amount of respiratory gas flowing through by unit of time, there being fundamentally a linear relationship. The evaporator is designed to provide water vapor with a temperature above 134° C., which heats the respiratory gas to the predetermined respiratory gas temperature when mixing with the respiratory gas to be humidified.

The design of the respiration humidifier according to the present invention is simple, which makes inexpensive manufacture possible. The respiratory gas and the relative humidity of the respiratory gas can be set independently from one another. The relative humidity of the respiratory gas is determined by the amount of water entering the evaporator per unit time and is then evaporated and fed into the respiratory gas flow per unit of time. The desired breathing gas temperature, which is set by mixing the respiratory gas to be humidified with the hot water vapor discharged from the evaporator, is used as the reference temperature for the relative humidity of the respiratory gas. The temperature of the water vapor must be sufficiently high for this, namely, higher than 134° C., and it can be set via the heating of the evaporator. An example of a thermodynamic calculation, which illustrates these relationships, will be described below. Since the water vapor reaches a maximum temperature of only 120° C. in the prior-art respiration humidifiers, the concept according to the present invention cannot be embodied with this.

The respiration humidifier according to the present invention can be designed without a great effort such that it guarantees a high level of hygiene. For example, a design of the respiration humidifier with, e.g., a hose pump (see below) as the metering means and with the evaporator arranged downstream is closed to the environment. Microorganisms cannot enter the sterile water container used as the water reservoir and into the flexible tube of the hose pump. Microorganisms can enter the respiration system through the opening during the standstill of the respiration humidifier only in the cold state. However, as soon as the respiration humidifier is again heated, all microorganisms are killed by the high heating temperature, which is above 134° C. under all operating conditions. (The hygienic regulations for steam sterilization specie that a generally and legally accepted reduction in the microorganism count is achieved if the microorganisms are exposed to a temperature of 134° C. for 3 minutes.)

In a preferred embodiment of the respiration humidifier, the evaporator has an interior space, which is closed with the exception of an inlet opening on its inlet side and an outlet opening on its outlet side, and which is partially or completely filled with a porous material. The closed design is advantageous for hygienic reasons, while the filling with a porous material leads to uniform generation of vapor, because the so-called Leidenfrost's phenomenon is prevented from occurring.

Leidenfrost's phenomenon occurs during the evaporation of water on hot surfaces. Vapor is formed under a drop of water, and this vapor carries the water drop and insulates it from the supply of more heat, so that it is suspended on the surface for a longer time. This effect may be very disturbing, because the evaporation may be retarded by it in time and it does not take place uniformly. An amount of water fed into an evaporator having a surface temperature exceeding 100° C. would evaporate in a pulsating manner, at times accompanied by hissing sounds. This problem is counteracted by means of a thin cannula in the respiration humidifier known from DE 43 12 793 C2. However, this cannula may easily become clogged; in addition, small drops, which will evaporate nonuniformly, are again also formed at the outlet of the cannula.

The problem caused by Leidenfrost's phenomenon is solved in the preferred embodiment of the present invention by the use of a very large surface, onto which the water is passed just below the evaporation temperature (100° C.). This is possible with various materials, which provide a large surface. Sintered glass, sintered ceramics, sintered steel, sintered copper, sintered brass, or even cooper wool are especially suitable materials for this. Even though sintered glass, sintered ceramic or sintered stainless steel do not have good thermal conductivity, these materials are especially suitable because they are anticorrosive. The poor thermal conduction is advantageous for the temperature gradient in the evaporator; the cold water can thus be admitted on the inlet side at a temperature between room temperature and a maximum of 99° C. without evaporating, and the superheated vapor can be removed on the outlet side at a temperature of, e.g., 140° C. to 300° C. without carrying water of condensation or aerosols with it.

A heat insulation is preferably provided between the outlet side of the evaporator and the respiratory gas channel, because the evaporator of the respiration humidifier is steadily maintained at a predetermined temperature, which is between 140° C. and 300° C. in the normal range of operation of the respiration humidifier, depending on the relative humidity and the temperature of the respiratory gas. Since the outlet opening of the evaporator preferably extends into the respiratory gas channel of the respiration system, a rather substantial amount of heat would be transferred onto the respiration system due to this connection and the heating in the absence of heat insulation. The dry respiratory gas would thus be heated even without the supply and evaporation of water, and an independent setting of the respiratory gas temperature and of the relative humidity of the respiratory gas would be more difficult. Due to the heat insulation between the outlet side of the evaporator and the respiratory gas channel, the heat conduction between the two elements is markedly reduced. Only the outlet opening of the evaporator extends into the respiration system. However, as soon as more water is evaporated, hardly any heat is released from this opening. Only small, convective heat components are left, which are negligible during normal operation.

The metering means preferably has a metering pump. In a preferred embodiment of the respiration humidifier according to the present invention, the metering pump has a hose pump, whose speed of rotation is adjustable and is in a functional connection with a flexible tube, which is or can be connected with one of its ends to a water reservoir and is in connection with the inlet side of the evaporator with its other end.

A respiration humidifier of such a design has practically no consumable parts any more, except for the water needed for the operation. The respiration humidifier is preferably supplied with sterile, mineral-free water via a flexible, commercially available bag (infusion bag), which is preferably connected to the respiration humidifier via a commercially available infusion set. The metering pump (hose pump or peristaltic pump), through which the flexible tube is led, is located between the bag and the evaporator. A possible wear of the tube by the hose pump can be counteracted by the tube being replaced after the bag has been emptied. Due to the system, this principle of humidification requires only low operating costs, which consist of the cost of water proper including the costs of packaging.

The hose pump may be manufactured for a long service life, which corresponds to the service life of the respiration humidifier. This also applies to the heater of the evaporator, which has practically no parts subject to wear.

The metering pump is preferably designed to run in the reverse direction to deliver a predetermined amount of water from the evaporator when the flow of the respiratory gas is interrupted. The metering pump may also be designed to run at a higher speed at the beginning of the flow of the respiratory gas to deliver a predetermined additional amount of water into the evaporator.

This design is used because, depending on the side of the structure, there is a certain amount of water in the evaporator on the cold side of the system. However, when the respiratory gas flow is interrupted, with a corresponding interruption of the water supply to the evaporator, part of this amount of water would continue to evaporate, because, e.g., the housing and the sintered material of the evaporator are at a high temperature and much heat is still being stored. This would lead to a continuation of the evaporation, which may be undesirable. For example, this water vapor would still be introduced into the respiration system and condense there. This amount of water would be taken up by the respiratory gas only when the flow of respiratory gas resumes.

This problem is solved in the preferred embodiment of the present invention by the metering pump running backward by an adjustable amount during the standstill of the flow of respiratory gas. During this backward running, the metering pump pumps the residual water out of the evaporator. Most of the amount of water is thus removed from the evaporator, and only the part of the water that is already in the superheater as vapor (i.e., in the area of the outlet side of the evaporator) can enter the respiration system. The dynamics of the respiration humidifier is improved as a result, and, e.g., the overshooting of the temperature after the standstill of the flow of respiratory gas, which is featured in all respiration humidifiers, is avoided.

In the same manner, the respiration humidifier can be brought more rapidly to a higher temperature by the metering pump delivering somewhat more water for a short time than is required by the water balance.

It would be possible, in principle, to operate the respiration humidifier according to the present invention without monitoring the temperature and/or the relative humidity of the respiratory gas, because if the amount of respiratory gas flowing through per unit of time and the initial humidity of the respiratory gas are known, the speed of rotation of the metering means and the heating capacity of the evaporator can be set such that the desired relative humidity of the respiratory gas and the desired temperature of the respiratory gas are obtained. However, a more reliable and simpler mode of operation of the respiration humidifier is achieved in a preferred embodiment by means of a control and regulating device, which is designed to control the metering means and the heater of the evaporator in response to predetermined values for the set points of the respiratory gas temperature and/or the relative humidity of the respiratory gas and to signals for the actual values of the respiratory gas temperature and/or the relative humidity of the respiratory gas. A temperature sensor connected to the control and regulating device for detecting the actual value of the temperature of the respiratory gas and a humidity sensor connected to the control and regulating device for detecting the actual value of the relative humidity of the respiratory gas are preferably provided.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENT

Figure 1:
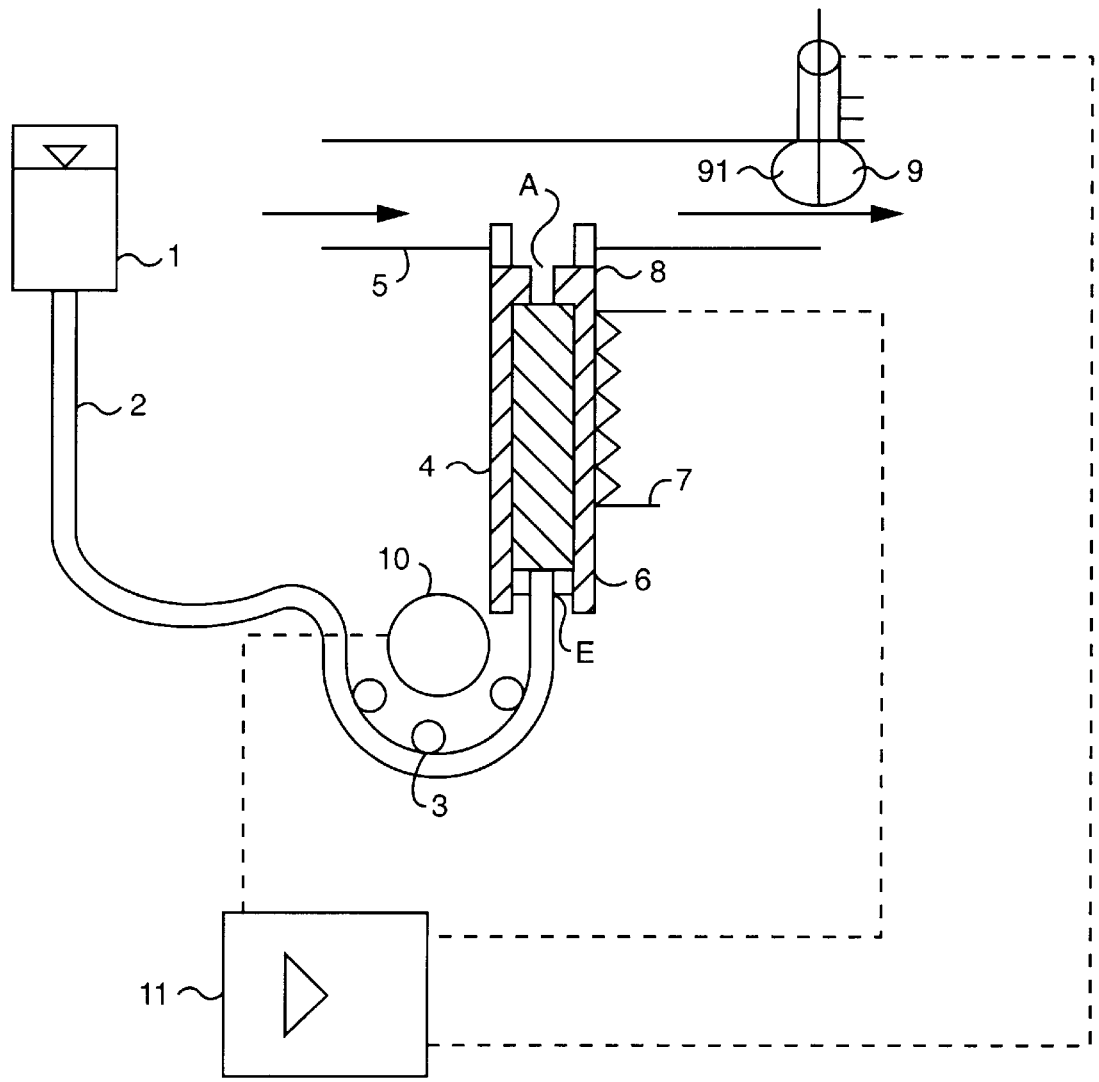
FIG. 1 is a schematic representation of an embodiment of the respiration humidifier according to the present invention.

A thermodynamic investigation is first provided, which illustrates the principles of the mode of operation of the respiration humidifier based on an example. It will show how the amount of water needed to humidify the respiratory gas per unit of time is metered correctly according to the present invention corresponding to the amount of respiratory gas (respiratory gas flow) per unit of time, so that any desired humidity can be obtained in the respiratory gas. The desired temperature of the respiratory gas can be set independently from this by adjusting the heating temperature of the evaporator.

It can be calculated by the thermodynamic investigation of the humidification that a saturated wet vapor or superheated vapor temperature of 120° C. is not sufficient to heat respiratory gas from, e.g., 25° C. to 37° C. and to humidify it at about 100% at the same time. The temperature is much too low for this. Thus, an undesired condensation may occur in prior-art respiration humidifiers operating at an evaporator temperature of 120° C.

If condensation is to be prevented, a vapor temperature of, e.g., 250° C. must be generated. The respiratory gas is heated from, e.g., 25° C. to 37° C. with the enthalpy of the vapor without part of the vapor condensing. There is, in general, a simple proportional relationship between the amount of water needed for the humidification per unit of time and the amount of respiratory gas flowing through per unit of time (respiratory gas flow rate). The following numerical example is presented for further explanation.

a) Calculation of the Necessary Amount of Water

The amount of water needed for the humidification of the respiratory gas per unit of time (dx/dt) is obtained from the absolute percentage of water (w) in the respiratory gas and the respiratory gas flow rate (dV/dt):

$$dx/dt = dV/dt \cdot w$$

As is seen from the equation, dx/dt is proportional to the respiratory gas flow rate, i.e., it can be set in a very simple manner via a proportional control.

At 100% relative humidity, air (used as the usual respiratory gas) is able to take up 42.5 mg of water per L under normal air pressure. Now, a relative humidity of 50% corresponds to half of this amount of water (21.25 mg/L).

At a respiratory gas flow rate of 10 L/minute, the following amount of water is needed for humidification to 100% relative humidity:

$$dx/dt = dV/dt \cdot w = 10 \text{ L/minute} \cdot 42.5 \text{ mg of water/L} =$$

$$= 425 \text{ mg/minute}$$

The absolute percentages of water increase and decrease at higher or lower respiratory gas temperatures according to the vapor pressure table for humid air. This can be taken into account in the algorithm for the humidification correspondingly.

b) Necessary Vapor Temperature

The following amount of heat is needed to heat the respiratory gas (air) from 25° C. to 37° C.:

Enthalpy $h_L = m_L \cdot C_{pL} \cdot \text{delta } T_L$ $$h_L = 1 \text{ g} \cdot 1.005 \text{ J/(g} \cdot \text{K)} \cdot 12 \text{ K} = 12.06 \text{ J (per g of air)}$$

Necessary vapor temperature for heating the air:

$$h_L = h_D = m_D \cdot C_{pD} \cdot \text{delta } T_D = 12.06 \text{ J (per g of air)}$$

With $C_{pD} = 1.85$ J/(g·K) and $m_D = 42$ mg of water per g of water, we obtain:

$$\text{delta } T_D = h_L/(m_D \cdot C_{pD}) = 12.06 \cdot 10^3 \text{ J} \cdot \text{g} \cdot \text{K)}/(42 \text{ g} \cdot 1.85 \text{ J}) =$$

$$= 0.15 \cdot 10^3 \text{ K} = 150 \text{ K}$$

Necessary vapor temperature $T_D$ = respiratory gas temperature +150 K

Using this thermodynamic equation, it is also possible to set up an error calculation. A change by 12.5 K in the vapor temperature leads to a change in the air temperature by 1 K. This means that the respiratory gas temperature can be controlled linearly by means of the vapor temperature.

If a relative humidity lower than 100% is desired, the enthalpy needed for heating the air must be supplied at a higher vapor temperature. For example, the vapor temperature must be increased by about 15 K at a 10% lower humidity of the respiratory gas in order to reach the same respiratory gas temperature.

Referring to the drawings in particular, FIG. 1 shows a schematic view of an embodiment of the respiration humidifier according to the present invention.

A commercially available water bag 1, e.g., an infusion bag containing deionized water, is used as a water reservoir and is connected to the respiratory gas via a connection tube 2, which may be designed as a commercially available infusion set. The water bag is arranged outside the housing of the respiration humidifier, which housing is not shown in FIG. 1, but may also be arranged within the housing in a compartment provided for that purpose.

The connection tube 2 leads to a flexible tube, which is led through a hose pump (peristaltic pump) 3 driven by a pump drive 10. The speed of rotation of the pump drive 10 is adjustable (also reversible in the exemplary embodiment) and is adjusted to the amount of water to be delivered per unit of time. The connection tube 2 may be made in one piece with the flexible tube led through the hose pump 3. The flexible tube opens into the inlet opening E of an evaporator 4.

In the exemplary embodiment, the evaporator 4 has a cylindrical housing, on the outside of which an electrically operated heater 7 is arranged. Fine-pored sintered material 6 is contained in the interior space of the housing of the evaporator 4. In the vicinity of the outlet opening A of the evaporator 4, the housing of the evaporator 4 is joined by a tubular heat insulation element 8, which is used as a connection between the evaporator 4 and a respiratory gas channel 5 of the respiratory gas system, with which the respiration humidifier is operated.

The water entering the evaporator 4 via the inlet opening E is evaporated in the lower area of the evaporator 4, and the vapor, rising upward, is heated further, so that it reaches a temperature markedly exceeding 100° C. and is consequently superheated (i.e., not saturated). The upper area of the evaporator 4 consequently acts as a superheater. The sintered material prevents Leidenfrost's phenomenon from occurring (see above).

The part of the respiratory gas channel 5 shown in FIG. 1 is preferably a part of the respiration humidifier, and additional components of the respiratory gas system, which are not the subject of the present application, are coupled with this part in order to connect the respiration humidifier to the respiratory gas system. However, it is also conceivable that the respiration humidifier ends at the heat insulation 8 and is connected to the respiratory gas system at a connection point coordinated with it.

Figure 2:
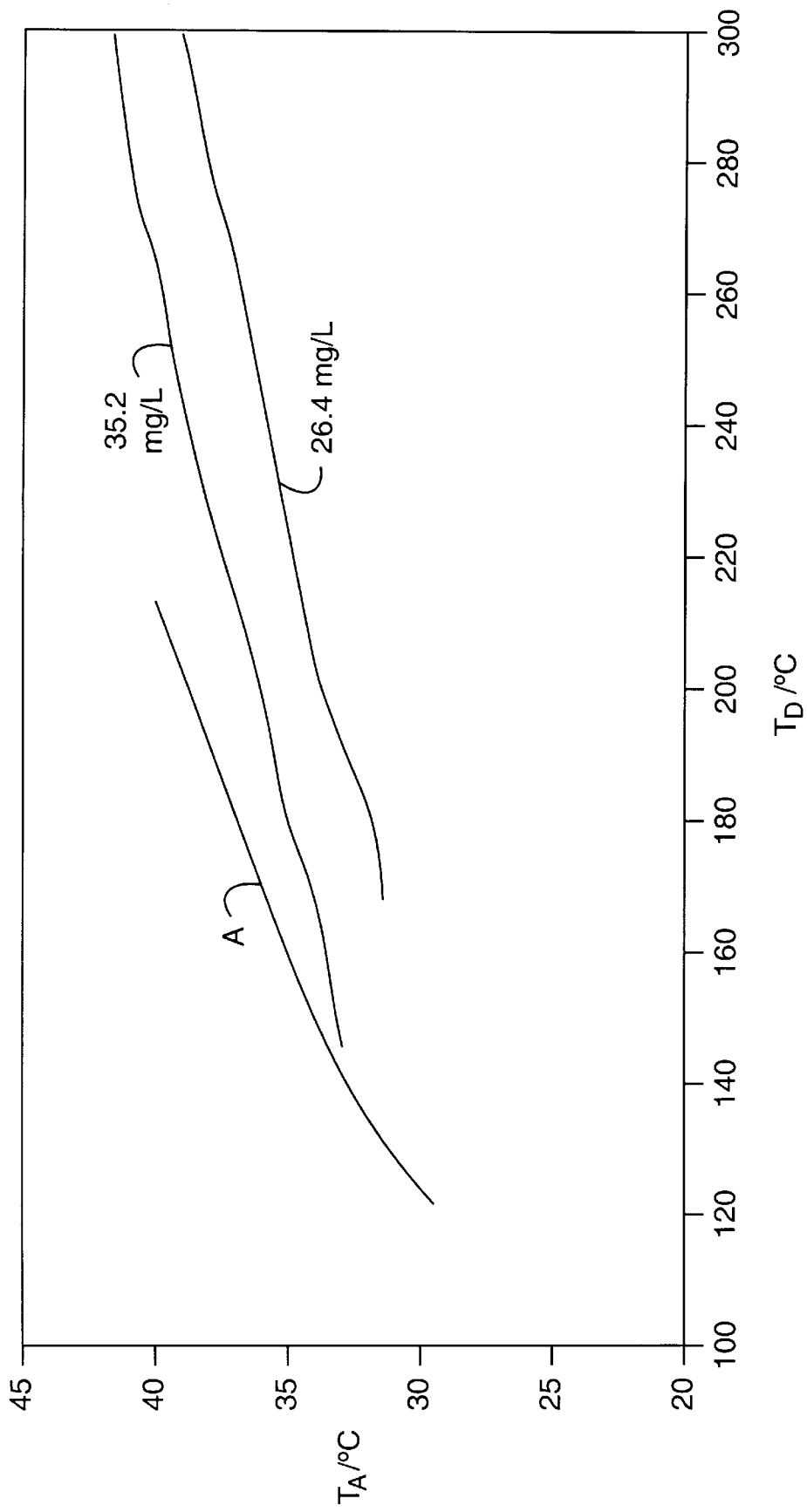
FIG. 2 is a graphic representation of the dependence of the temperature of the respiratory gas on the heating temperature of the evaporator for two different absolute percentages of water in the respiratory gas for a constant respiratory gas flow rate of 30 L/minute.

As is seen from the above thermodynamic calculation, independent control of the humidity and temperature of the respiratory gas can be achieved with this arrangement by varying the amount of water metered and by varying the temperature of the vapor. As is shown in FIG. 2, this dependence is confirmed by laboratory experiments.

Corresponding to the value of the flow rate of the respiratory gas, the amount of water needed per unit of time is added proportionally via a pump (hose pump 3). The relative humidity of the respiratory gas is obtained simply from the above equation. Consequently, humidity measurement is not compulsory. However, a humidity sensor 9, which is preferably arranged on the outlet side of the respiratory gas channel 5, may be provided for displaying the real humidity and for correcting the control (see FIG. 1).

In the case of respiration blowers which make available the respiratory air from the ambient air and do not operate with a dry pressurized gas, the humidity present in the ambient air must be taken into account. Humidity measurement on the ambient side in front of the blower or in the respiratory gas channel 5 is suitable in such an arrangement for correcting the amount of water fed in per unit of time.

It is also conceivable to monitor the feed of water directly with a humidity sensor on the respiratory gas side (e.g., with the humidity sensor 9) and to control it by means of a proportional control. Now, the respiration humidifier is not dependent on knowing the flow rate of the respiratory gas of the respirator or the humidity in the environment (in the case of a respirator driven with a blower). The humidity signal is evaluated and the amount of water to be fed in per unit of time is increased until the desired relative humidity of the respiratory gas is reached at the desired respiratory gas temperature. As is seen in FIG. 2, the necessary temperature or output of the heater 7 can be inferred from the desired respiratory gas temperature, either based on the algorithms given above or by means of a corresponding family of characteristics.

The respiratory gas temperature is preferably measured at the end of the respiration humidifier (e.g., by means of a temperature sensor 91, which is designed as one assembly unit with the humidity sensor 9), and the heating output of the evaporator 4 is controlled by means of a controller. When the respiratory gas temperature decreases, the heating output is increased and the vapor temperature is thus increased until the desired respiratory gas temperature is again reached.

FIG. 1 schematically shows a control and regulating device 11, which regulates the speed of rotation of the hose pump 3 and the output of the heater 7 in response to signals for the actual values of the respiratory gas temperature and the relative humidity of the respiratory gas from the combined temperature sensor 91 and humidity sensor 9. The set points may be predetermined for the control and regulating device 11. The control and regulating device 11 optionally also controls the reverse rotation or the high-speed rotation of the hose pump 3 during the interruption or start of the flow of respiratory gas, as was explained above.

Values with tolerances, especially an only inaccurately known or varying delivery capacity of the metering means, or deviations in the flow rate of the respiratory gas, must be expected to occur during the use of the respiration humidifier under real conditions. For example, the amount of water fed into the evaporator per unit of time or the predetermined value or the measured value of the respiratory gas flow rate, but also the heating temperature, may thus consequently be incorrect within respective tolerance ranges. In the ideal case, the respiratory gas temperature and the relative humidity of the respiratory gas can be adjusted correctly if a precision temperature sensor and a precision humidity sensor are available in the area of the heated and humidified respiratory gas.

However, humidity sensors are, in particular, expensive and often inaccurate. Furthermore, the condensation of water at the humidity sensor makes a relevant measurement of the relative humidity of the respiratory gas impossible. Possibilities of how the respiration humidifier can be operated in a reliable manner even without a humidity sensor and how a constant humidity can nevertheless be maintained will therefore be described below.

An examination of the system from the viewpoint of the above-mentioned tolerances shows essentially two possibilities of compensation.

(1) The respiratory gas temperature at the outlet of the respiration humidifier shall be maintained at a set point. If there are errors in the determination of the flow rate of the respiratory gas and/or in the amount of water metered, the respiratory gas temperature will change. The respiratory gas temperature can be adjusted by correspondingly increasing or decreasing the heating temperature, i.e., the vapor temperature.

The respiratory gas temperature can consequently be controlled by varying the value of the heating temperature. Since the true values of the respiratory gas flow rate and the amount of water being metered have tolerances (measurement and metering errors), the relative humidity of the respiratory gas may deviate from the desired setting. Example: If the respiratory gas flow rate is higher by +10% and the amount of water fed into the evaporator per unit of time is lower by −10%, the relative humidity of the respiratory gas deviates from the set point by about −15%.

(2) Another possibility is to change the amount of water fed into the evaporator per unit of time corresponding to the deviation of the respiratory gas temperature from the set point. This presupposes that the heating temperature has only a small error and that the water vapor released from the evaporator assumes the heating temperature (both conditions are usually met in practice). Deviations of the respiratory gas temperature can be attributed in this case to an incorrect metering of the amount of water fed into the evaporator per unit of time only and can be used for control.

To do so, the heating or water vapor temperature is first determined by calculation on the basis of the thermodynamic formulas, as was described above, and the amount of water to be fed into the evaporator per unit of time is determined corresponding to the predetermined respiratory gas flow rate. In the case of deviations of the respiratory gas temperature from the set point, the necessary change in the amount of water metered can be calculated from an investigation of the enthalpy changes by setting up the equations $$m_L * C_{pL} * \text{delta } T_L = h_L = h_D = m_D * C_{pD} * \text{delta } T_D$$

for the actual values and for the set points and dividing them by one another. We obtain:

$$m_D(\text{set}) = m_D(\text{actual}) * \frac{(T_{Ls} - T_0) * (T_D - T_{Li})}{(T_D - T_{Ls}) * (T_{Li} - T_0)}$$

in which $T_{Ls}$=temperature set point of the respiratory gas
$T_{Li}$=actual temperature of the respiratory gas
$T_0$=actual temperature before the respiration humidifier
$T_D$=water vapor temperature (hot vapor)

The respiratory gas temperature can consequently be set by changing the amount of water metered, i.e., the amount of water fed into the evaporator per unit of time. Control in the conventional sense of the word is not necessary. Any deviation of the respiratory gas temperature from the set point leads to a new determination (setting) of a changed amount of water metered.

The relative humidity of the respiratory gas now remains constant even if there is an error in the values for the respiratory gas flow rate and the amount of water metered. Example: In the case of a deviation in the respiratory gas flow rate by 10% and in the amount of water fed into the evaporator per unit of time by −10%, the metering of water is compensated corresponding to the above equation. Both the respiratory gas temperature and the relative humidity of the respiratory gas reach their respective set points.

By calculating the water vapor temperature and the amount of water to be metered in advance and correspondingly compensating them based on the respiratory gas temperature reached, a highly reliable and accurate humidification of the respiratory gas can be performed. The following advantages are obtained:

The relative humidity of the respiratory gas can be determined accurately and can be displayed for the user without having to measure the humidity of the respiratory gas proper.

Condensation of water vapor in the breathing tubes can thus be reliably prevented from occurring.

The tolerances that become established in the real case of application are compensated by the calculation described based on the set/actual enthalpy ratios.

The temperature before the respiration humidifier ($T_0$) must be measured for the accurate advance determination of the respiratory gas temperature. This can be performed with a simple temperature sensor (e.g., Pt 100, NTC) inexpensively and reliably.

FIGS. 2 through 5 show measurement results obtained with a prototype of the respiration humidifier. AR measured values were measured directly behind the respiration humidifier, without the use of a tube system. All characteristics of the respiration humidifier can thus be better analyzed. More sluggish behaviors can, in general, be recognized in the case of practical application with a tube system.

Figure 3:
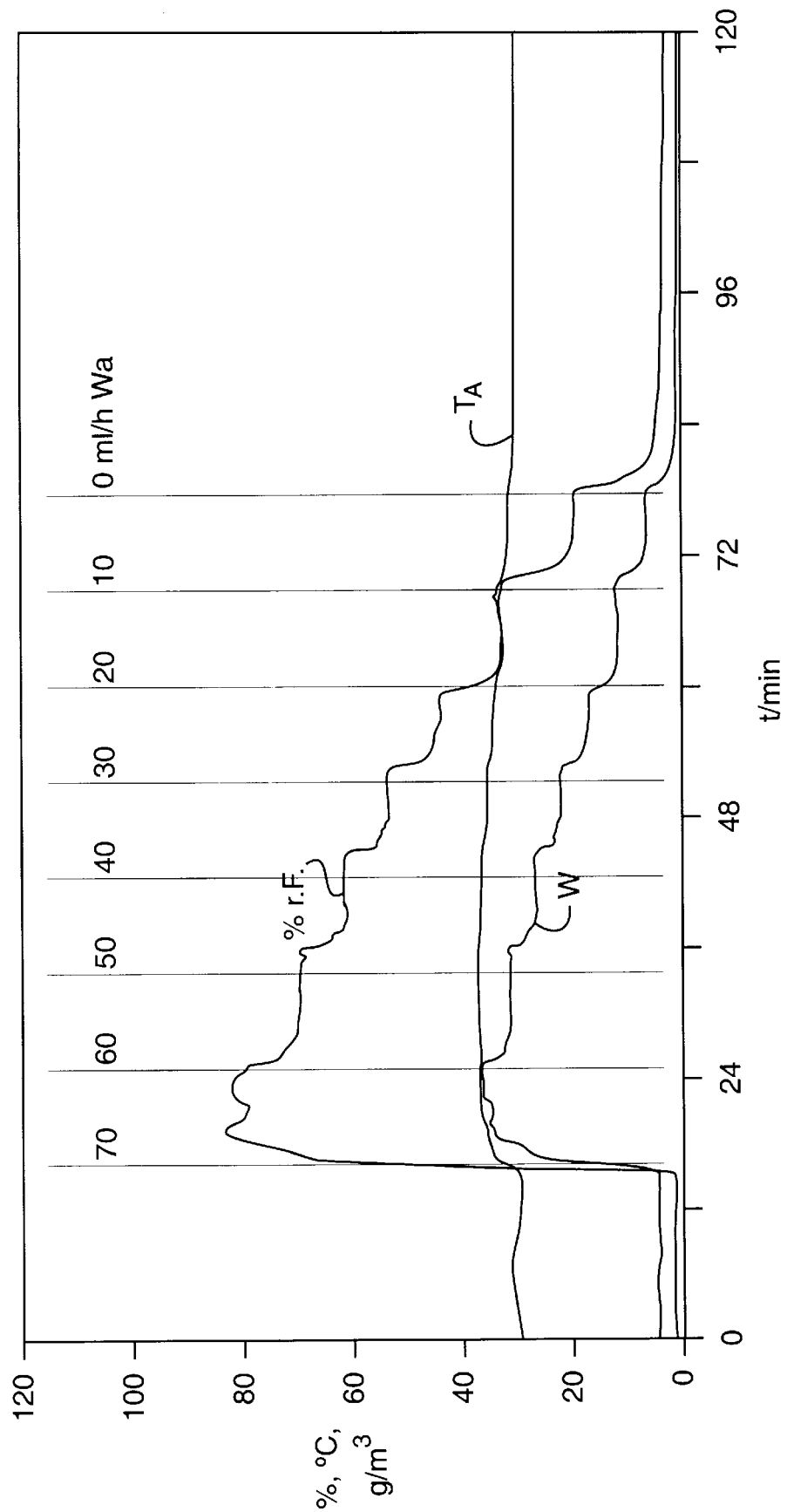
FIG. 3 is a graphic representation of the curves describing the temperature of the respiratory gas, the absolute percentage of water in the respiratory gas, and the relative humidity of the respiratory gas for a constant respiratory gas flow rate of 30 L/minute with stepwise reduction in the amount of water fed to the evaporator per unit of time.

FIG. 3 shows the curves of the respiratory gas temperature $T_A$ (° C.), the percentage of water w (g/m$^3$), and the relative humidity (% RH) for different amounts of water metered for a constant respiratory gas flow rate of 30 L/minute. It is seen that when the amount of water metered is reduced stepwise from 70 mL/hour to 0 mL/hour of water (Wa) in steps of 10 mL/hour, the relative humidity of the respiratory gas and the percentage of water decrease stepwise. The respiratory gas temperature $T_A$ also decreases somewhat, as is shown by the thermodynamic calculation. The heating temperature was maintained at a constant value of 250° C. in this design. If the respiratory gas temperature is to be controlled to a constant value, the heating temperature should have been increased stepwise.

Figure 4:
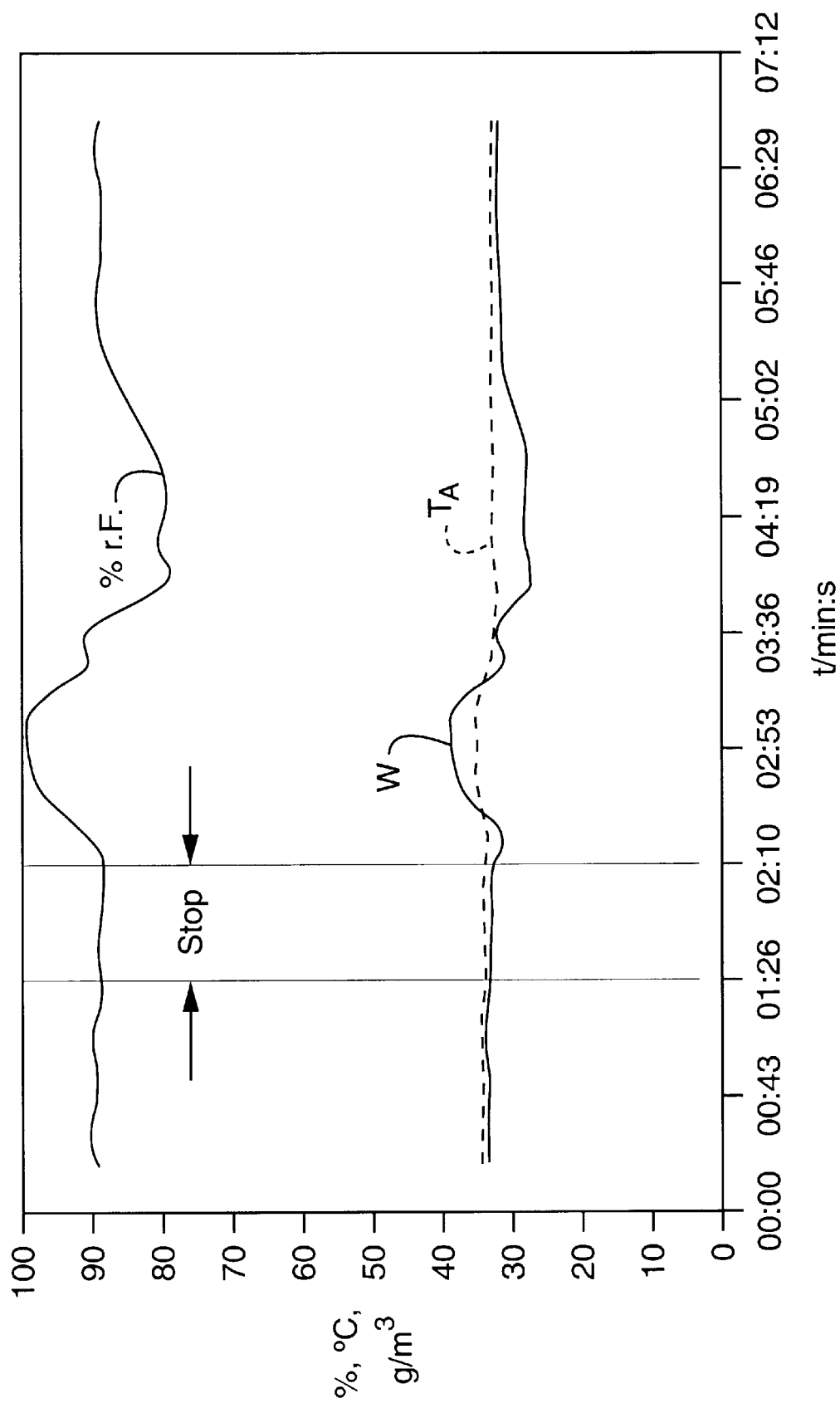
FIG. 4 is a graphic representation of the curves describing the temperature of the respiratory gas, the absolute percentage of water in the respiratory gas, and the relative humidity of the respiratory gas during interruption of the respiratory gas flow rate of 30 L/minute for 1 minute.

FIG. 4 shows the changes over time in the case of an interruption in the respiratory gas flow rate of 30 L/minute for about 45 sec. After the respiratory gas flow is restarted, the relative humidity of the respiratory gas and the percentage of water increase for about 30 sec. This affects the respiratory gas temperature $T_A$ only slightly.

Figure 5:
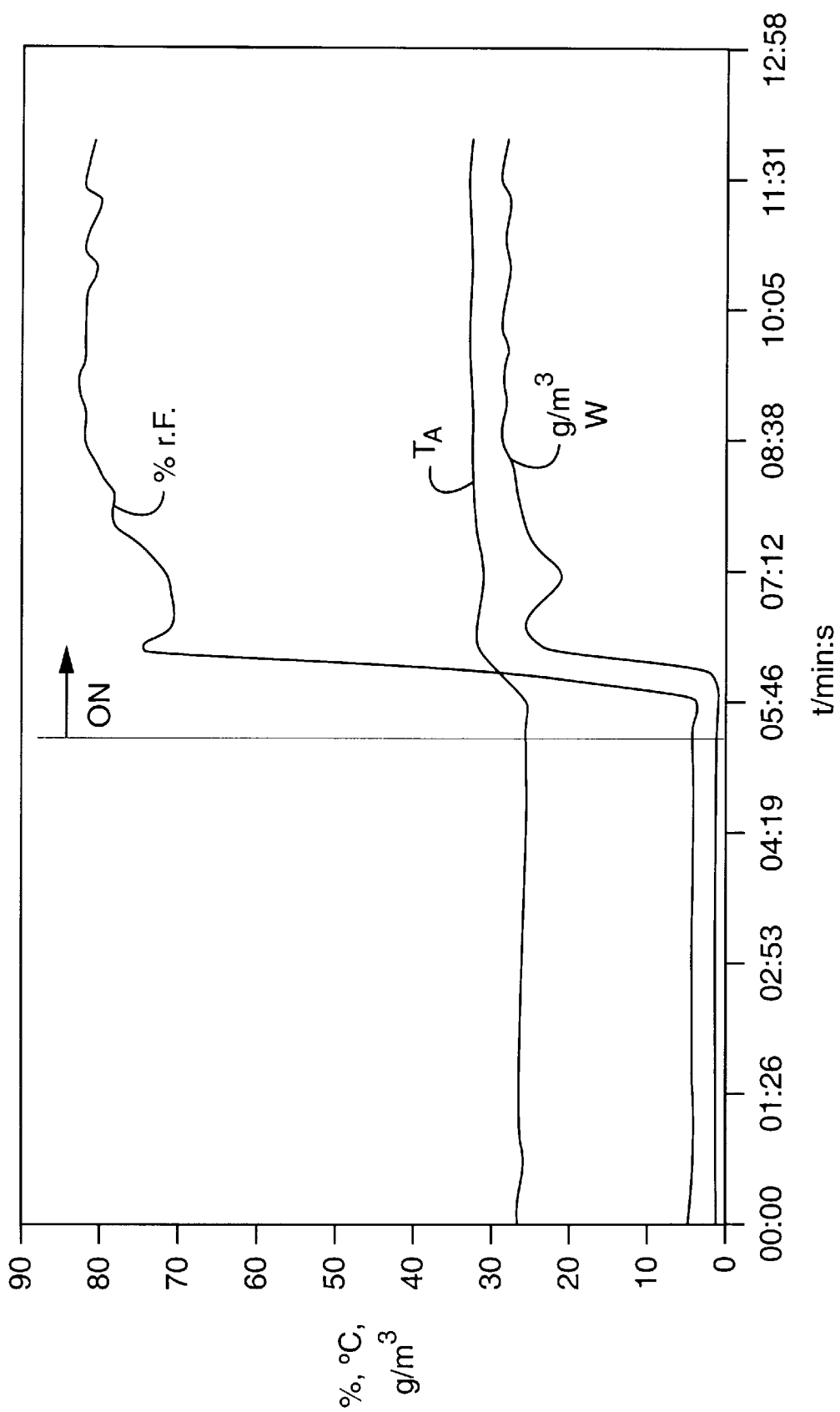
FIG. 5 is a graphic representation of the curves describing the temperature of the respiratory gas, the absolute percentage of water in the respiratory gas and the relative humidity of the respiratory gas at the startup of the respiration humidifier.

FIG. 5 shows the changes over time upon the switching on of the respiration humidifier to a respiratory gas flow rate of 30 L/minute and with preheated evaporator. The respiration humidifier is very rapid compared with prior-art systems, which require, on the average, 10 to 30 minutes to reach the desired respiratory gas temperature $T_A$. The respiration humidifier according to the present invention requires only 3 minutes to reach its maximum output.

FIG. 2 shows the respiratory gas temperature $T_A$ as a function of the heating temperature $T_D$ for two different percentages of water at a respiratory gas flow rate of 30 L/minute. It can be recognized from this figure that the respiration humidifier behaves as expected based on the theory of thermodynamics. Both parameters, namely, the respiratory gas temperature and the relative humidity of the respiratory gas, can be set independently from one another and be made available for the respiratory gas system. Curve A shows the limit between the condensation range (left) and the vapor range (right).

In summary, the respiration humidifier according to the present invention consequently has a very simple design and can be manufactured at a low cost.

The respiration humidifier may be designed practically without wear parts that must be replaced or cleaned and sterilized at regular intervals, as in the prior-art systems. The operating costs are therefore low.

The respiration humidifier may use a closed, sterile water supply, which prevents contamination with microorganisms. The respiration humidifier itself operates with temperatures that are above the known sterilization temperature of 134° C. Even in the case of prolonged standstill of the respiration humidifier, infestation with microorganisms can occur in the evaporator/superheater only, but this sterilizes itself immediately upon startup. The respiration humidifier would sterilize itself even if water contaminated with microorganisms were used, so that the patient is always protected hygienically.

The respiratory gas temperature and the relative humidity of the respiratory gas can be controlled independently. The respiratory gas temperature is controlled by varying the heating output of the evaporator, and the relative humidity of the respiratory gas can be controlled by varying the amount of water metered into the evaporator per unit of time.

Superheating phenomena ("hot spots") during the standstill of the respiratory gas flow and long heat-up times can be eliminated by a special dynamics of the metering of water, e.g., by the metering pump delivering water backward during the standstill of the respiratory gas flow.

While specific embodiments of the invention have been shown and described in detail to illustrate the application of the principles of the invention, it will be understood that the invention may be embodied otherwise without departing from such principles.

What is claimed is:

1. A respiration humidifier for use with a respiratory gas channel flowing respiratory gas, the respiration humidifier comprising:
a metering device for feeding water; and
an electrically heated evaporator having an inlet and an outlet, said inlet having a connection with said metering device and said outlet being connectable to the respiratory gas channel, said metering device providing a water feed in an amount to control a relative humidity of the respiratory gas at a predetermined respiratory gas temperature to said evaporator per unit of time as a function of an amount of respiratory gas flowing through per unit of time, and said evaporator providing water vapor and controlling a water vapor temperature above 134° C., to heat the respiratory gas and control a temperature of the respiratory gas on mixing of the water vapor with the respiratory gas.

2. The respiration humidifier in accordance with claim 1, wherein said evaporator has structure defining a closed interior space with only an inlet opening providing said inlet and an outlet opening providing said outlet, said closed interior space being one of partially or completely filled with porous material.

3. The respiration humidifier in accordance with claim 2, wherein said porous material is one of a sintered material and copper wool.

4. The respiration humidifier in accordance with claim 1, further comprising:
heat insulation between said outlet of said evaporator and said respiratory gas channel.

5. The respiration humidifier in accordance with claim 1, wherein said metering device has a metering pump.

6. The respiration humidifier in accordance with claim 5, wherein said metering pump runs backwards for delivery of a predetermined amount of water from said evaporator to remove said predetermined amount of water from said evaporator in case of an interruption in said flow of said respiratory gas.

7. The respiration humidifier in accordance with claim 5, wherein said metering pump runs faster at a beginning of said flow of said respiratory gas to deliver a predetermined additional amount of water into said evaporator.

8. The respiration humidifier in accordance with claim 5, further comprising;
a flexible tube;
a water reservoir connected to said flexible tube, wherein said metering pump is a hose pump with a speed of rotation which is adjustable and which is in functional connection with said flexible tube, an end of said flexible tube being connected to said inlet of said evaporator.

9. The respiration humidifier in accordance with claim 1, further comprising:
a control and regulating device for controlling said metering means and a heater of said evaporator in response to predetermined values for set points of said respiratory gas temperature and/or said relative humidity of said respiratory gas and to signals for actual values of said respiratory gas temperature and/or relative humidity of said respiratory gas.

10. The respiration humidifier in accordance with claim 9, further comprising:
a temperature sensor connected to said control and regulating device for detecting said actual value of said respiratory gas temperature.

11. The respiration humidifier in accordance with claim 9, further comprising:
a humidity sensor connected to said control and regulating device (11) for detecting said actual value of said relative humidity of said respiratory gas.

12. The respiration humidifier in accordance with claim 9, wherein said control and regulating device adjusts a setting of said amount of water $m_D$ fed to said evaporator per unit of time in case of a deviation of said measured actual value $T_{Li}$ of said respiratory gas temperature from said known set point $T_{Ls}$ according to the equation:

$$m_D(\text{set}) = m_D(\text{actual}) * \frac{(T_{Ls} - T_0)*(T_D - T_{Li})}{(T_D - T_{Ls})*(T_{Li} - T_0)}$$

wherein said values $T_0$ for said actual temperature upstream of said respiration humidifier and $T_D$ for said water vapor temperature are known to said control and regulating device.

13. A respiration system for flowing respiratory gas, comprising:
a respiratory gas channel through which the respiratory gas flows;
an evaporator having an inlet and an outlet, said outlet having a connection to said respiratory gas channel, and said evaporator receiving water from said inlet and heating the water to provide water vapor at a water vapor temperature above 134° C., said evaporator mixing said water vapor with the respiratory gas in said respiratory gas channel to form humidified respiratory gas, said evaporator controlling a temperature of said humidified respiratory gas by controlling heating of said water vapor;
a metering device feeding water to said inlet of said evaporator, said metering device controlling a humidity of said humidified respiratory gas by controlling a rate of water feed to said evaporator.

14. The respiration system in accordance with claim 13, wherein said evaporator has structure defining a closed interior space with only an inlet opening providing said inlet and an outlet opening providing said outlet, said closed interior space being one of partially or completely filled with porous material wherein said porous material is one of a sintered material and copper wool.

15. The respiration system in accordance with claim 13, further comprising:
heat insulation between said outlet of said evaporator and said respiratory gas channel.

16. The system in accordance with claim 13, further comprising:
a temperature sensor for measuring said temperature of said humidified respiratory gas;
a humidity sensor for measuring said humidity of said humidified respiratory gas;
a control device connected to said metering device and to said evaporator for comparing said temperature of said humidified respiratory gas to a desired temperature and adjusting said evaporator to minimize a difference between said temperature of said humidified respiratory gas and said desired temperature, said control device comparing said humidity of said humidified respiratory gas to a desired humidity and adjusting said metering device to minimize a difference between said humidity of said humidified respiratory gas and said desired humidity.

17. A respiration process comprising the steps of:

providing a respiratory gas channel;

flowing respiratory gas in the respiratory gas channel;

providing a heated evaporator having an inlet and an outlet, said outlet being in communication with the respiratory gas channel;

feeding water to said inlet of said evaporator;

heating the water in said evaporator to evaporate the water into water vapor and raise the temperature of the water vapor to a water vapor temperature;

mixing the water vapor and the respiratory gas to create a humidified respiratory gas at a mixed humidity and at a mixed temperature;

controlling said mixed humidity of said humidified respiratory gas by controlling said feeding of water;

controlling said mixed temperature of said humidified respiratory gas by controlling said heating of said water vapor.

18. The respiration process according to claim 17, wherein; said controlling adjusts an amount of water $m_D$ fed to the evaporator per unit of time in case of a deviation of the measured actual value $T_{Li}$ of the respiratory gas temperature from a known set point $T_{Ls}$ according to the equation:

$$m_D(\text{set}) = m_D(\text{actual}) * \frac{(T_{Ls} - T_0)*(T_D - T_{Li})}{(T_D - T_{Ls})*(T_{Li} - T_0)}$$

wherein a value $T_0$ for an actual temperature upstream of the respiration humidifier and $T_D$ for the water vapor temperature are known.

19. The method in accordance with claim 17, wherein:

said controlling of said mixed humidity includes, determining a desired humidity and a desired temperature of said humidified respiratory gas, determining a desired rate of water needed to create said humidified respiratory gas at said desired humidity and at said desired temperature, and feeding the water into said evaporator at said desired rate.

20. The method in accordance with claim 17, wherein:

said controlling of said mixed temperature includes, determining a desired humidity and a desired temperature of said humidified respiratory gas, determining a desired amount of heating needed to create said humidified respiratory gas at said desired humidity and at said desired temperature, heating the water vapor at said desired amount.

21. The method in accordance with claim 17, wherein:

said heating creates substantially pure water water and heats the water vapor to above 134 degrees C.;

said mixing creates said mixed temperature by transferring heat from the water vapor to the respiratory gas;

said mixing creates said mixed humidity by transferring humidity from the water vapor to the respiratory gas.

* * * * *